United States Patent
Wu et al.

(10) Patent No.: US 10,198,165 B2
(45) Date of Patent: Feb. 5, 2019

(54) SYSTEM AND METHOD OF MAPPING MEDICAL IMAGE OF SINGLE HEART CHAMBER

(71) Applicant: NATIONAL YANG-MING UNIVERSITY, Taipei (TW)

(72) Inventors: Tung-Hsin Wu, Taipei (TW); Jing-Yi Sun, Taipei (TW); Chun-Ho Yun, Taipei (TW); Chung-Lieh Hung, Taipei (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 236 days.

(21) Appl. No.: 15/203,472

(22) Filed: Jul. 6, 2016

(65) Prior Publication Data

US 2017/0199654 A1    Jul. 13, 2017

(30) Foreign Application Priority Data

Jan. 8, 2016 (TW) .............................. 105100587 A (51) Int. Cl.
*G06F 3/0484* (2013.01)
*G06F 3/0481* (2013.01)
(Continued)

(52) U.S. Cl.
CPC ........ *G06F 3/04845* (2013.01); *A61B 5/0044* (2013.01); *A61B 5/055* (2013.01); *A61B 6/032* (2013.01); *A61B 6/503* (2013.01); *G06F 3/04815* (2013.01); *G06T 3/0037* (2013.01); *G06T 11/001* (2013.01); *G06T 11/003* (2013.01); *G06T 19/20* (2013.01);
(Continued)

(58) Field of Classification Search
None
See application file for complete search history.

(56) References Cited

U.S. PATENT DOCUMENTS

2005/0119553 A1   6/2005   Pedrizzetti et al.
2008/0137934 A1*   6/2008   Sakaguchi ........... A61B 6/4441
                                                              382/132
(Continued)

FOREIGN PATENT DOCUMENTS

TW            I448986 B      8/2014

OTHER PUBLICATIONS

"MedDream WEB DICOM Viewer User's Manual (version 4.03)", published by Softneta, published in 2014, updated on Apr. 12, 2015.*

*Primary Examiner* — Zhengxi Liu
(74) *Attorney, Agent, or Firm* — Muncy, Geissler, Olds & Lowe, P.C.

(57) ABSTRACT

A system of mapping a cardiac image of single heart chamber and a method thereof are disclosed. In the system and method thereof, one heart chamber (such as a left atrium, a left ventricular, a right atrium, right ventricular or aortic structure) can be selected in a 3D-based cardiac image (such as a CT or MRI image), and slices of the selected heart chamber are reconstructed and unwrapped by a 2D mapping visual display manner. The visual display and required angle alignment planes for subsequent analysis will be adjusted and achieved by operator manually, with specific global and regional architectural analysis performed by automatic algorithm.

13 Claims, 12 Drawing Sheets

(51) Int. Cl.
*A61B 5/055* (2006.01)
*G06T 11/00* (2006.01)
*G06T 19/20* (2011.01)
*A61B 5/00* (2006.01)
*A61B 6/03* (2006.01)
*A61B 6/00* (2006.01)
*G06T 3/00* (2006.01)

(52) U.S. Cl.
CPC ............... *A61B 2576/023* (2013.01); *G06F 2203/04803* (2013.01); *G06T 2207/10081* (2013.01); *G06T 2207/10088* (2013.01); *G06T 2207/30048* (2013.01)

(56) References Cited

U.S. PATENT DOCUMENTS

| | | | |
|---|---|---|---|
| 2015/0199840 A1 | 7/2015 | Hatanaka et al. | |
| 2015/0238149 A1* | 8/2015 | Nitta | A61B 5/055 600/413 |

\* cited by examiner

SYSTEM AND METHOD OF MAPPING MEDICAL IMAGE OF SINGLE HEART CHAMBER

BACKGROUND OF THE INVENTION

1. Field of the Invention

The present disclosure is related to a cardiac image rendering technology, more particularly to a system capable of providing an operator to select any specific chamber (a left atrium, a left ventricular, a right atrium or a right ventricular) from a heart from a three-dimension (3D) cardiac image or dataset (such as a CT or MRI image), and reconstruct the slices of the selected chamber and then unwrap into 2D map image display with pre-defined landmarks used for reference points by a mapping manner, and a method thereof.

2. Description of the Related Art

Heart diseases are generally classified as the diseases caused by the problem in intrinsic anatomic/functional abnormalities and the diseases caused by the problem in heart rhythms, the former is a kind of heart diseases caused by abnormal heart structure, for example, coronary heart diseases, valvular heart diseases, congenital heart diseases, cardiomyopathy, or heart failure; the latter includes supraventricular heart arrhythmias, atrial fibrillation (AF), ventricular tachycardia and so on. The heart chamber most likely has anatomical remodeling (such as change of chamber wall thickness or altered chamber volume) before any clinical symptom of any kind of heart diseases. Slice images of the heart can be obtained by using 3D-based medical imaging modalities, such as computed tomography (CT) modality or magnetic resonance imaging (MRI) modality, and extent of morphological changes or alterations of the heart can be identified or even quantified from the slice images. However, the slice images are grayscale and no obvious delineations between regions of architectural changes or any given chambers adjacent to each other can be steadily shown in the slice image. Though a very drastic change of the heart chamber can be obviously observed or recognized in the sectional image, but it could be challenging to intuitively interpret detailed or regional morphological information or spatial information (such as gross morphology of single heart chamber, local myocardial wall thickness of single heart chamber, wall thickness heterogeneity, or comparison between morphology changes at different times) on the slice images. However, above-mentioned information carries fundamental basis for early detection of disease onset and recognition of disease course evolution and remodeling for heart diseases. While most of current medical imaging modalities have the basic function of generating 3D or 4D format for clinical use, image-based information overload and burden may sometimes result in more complex and excessive clinical data in return, with certain degree of misjudgment. On the other hand, some key information can not be displayed and elaborated very well in an efficient way. In particular, for morphological descriptions of any single heart chamber or structural entity, current 3D- or 4D-based image analysis results cannot meet the requirement for clinic purpose.

SUMMARY OF THE INVENTION

In order to circumvent the problem that current cardiac image and post-processing technology or software package fails to provide the gross and comprehensive morphological information of any single heart chamber, the objective of the present disclosure is to provide a visual system of mapping the medical image of any single heart chamber by a 2D display, and a method thereof. The system uses the cardiac image (such as CT or MRI cardiac image) to generate projection of morphology and spatial information of any single heart chamber (such as the left atrium, left ventricular, right atrium, right ventricular or large aortic structure), and then unwrap the morphology and spatial information by a 2D mapping manner, with specific anatomic landmarks provided as reference.

To achieve the objective, the present disclosure provides a system of mapping medical image of any single heart chamber, and the system includes a medical image interactive interface, an image pre-processing unit, a projection unwrapping point recording unit, a slice setting unit, a division processing unit, a mapped image establishment unit and an instant calculation unit.

The medical image interface is configured to display a cardiac image (a CT or MRI image) from a 3D-based medical image database, and express four-chamber view, two-chamber view and short axis view of the heart by displaying a horizontal view, a sagittal view or a coronal view of the medical image.

The image pre-processing unit includes an image adjustment module, an image angle correction module and an image coordinate correction module. The image adjustment module is configured to receive an image adjustment instruction (such as instruction for adjusting brightness or contrast of the image) imported or via input process by an operator, and adjusts the image according to the image adjustment instruction to make the contour of the heart chamber of each of the views of the medical image clearer. The image angle correction module is configured to receive an angle adjustment instruction imported or via input process by the operator through the medical image interface for alignment, and adjust each of the views of the medical image to a required angle according to the angle adjustment instruction. The image coordinate correction module is configured to receive a coordinate correction instruction inputted by the operator through the medical image interface, and correct coordinates of the four-chamber view, the two-chamber view and the short axis view according to the coordinate correction instruction.

The projection unwrapping point recording unit is configured to record a projection unwrapping point for any single heart chamber in the cardiac image, and the projection unwrapping point is set by the operator according to a coordinate axis of the medical image interface.

The slice setting unit includes an image rendering module, a slice setting interface and a slice recording module. The image rendering module is configured to render the sectional images processed by the image pre-processing unit into the slice setting interface for display, and the operator can input a first slice and a last slice of any single heart chamber through the slice setting interface. The slice recording module is configured to record the first slice, the last slice, and all slices between the first slice and the last slice.

The division processing unit includes a slice load module, a division interface and a sub-area processing module. The slice load module is configured to load the four-chamber view images corresponding to the recorded slices into the division interface. The operator manually performs chamber division on each of the loaded four-chamber view images. The operator can select a desired chamber first, and then input contour lines along border of the selected chamber on each of the loaded view images, so as to form a sub-area on each of the loaded view images. The sub-area processing module is configured to calculate inner and outer borders of each of sub-areas of the view images by using well-known method, such as contour interpolation method, active contour method, border dilation method, border shrink method, seeded region grow method, volume calculation method or distance calculation method, and then calculate a myocardial wall thickness and a chamber volume of the chamber and accumulate the chamber volume to obtain a chamber capacity according to information of the inner and outer borders.

The mapped image establishment unit includes an image reconstruction module, a chamber map display interface and a chamber map expression module. The image reconstruction module is configured to unwrap a 3D medicine image of any single heart chamber into a 2D chamber map image of any single heart chamber by using projection manner and a calculation function (such as geometric projection method or mathematic analysis method), and according to the projection unwrapping point and the information of all sub-areas. The image reconstruction module further displays the chamber map image and factual data including volume of the chamber, mass and thickness of myocardial wall, wall thickness heterogeneity and morphology change, on the chamber map display interface by inner-built, automatic algorithm. Moreover, the chamber map expression module can display a grayscale chamber map image, a color chamber map image and a chamber contour map image to facilitate an interpreter to interpret thinness of the chamber wall, locations of blood vessel and valve, and so on.

The instant calculation unit is configured to calculate and display morphology data of a region of interest (ROI), and the ROI is instantly selected by the operator in the chamber map image.

The present disclosure further provides a method of mapping a cardiac image of single heart chamber, and the method includes following steps:

In step one, a cardiac image is acquired from a remote medical image database and loaded into a system in a local smart device, and the medical image is displayed in a medical image interface of the system. The cardiac image can be a CT or MRI image. A four-chamber view, a two-chamber view and short axis view of heart can be expressed by a horizontal view, a sagittal view, and a coronal view of the medical image.

In step two, the operator can adjust and correct brightness, contrast, angle or coordinate of each of view images shown on the medical image interface by using an image preprocessing unit of the system, so as to adjust the coordinates and angles of the four-chamber view, the two-chamber view and the short axis view of the heart, to make the contour of the heart chamber clearer.

In step three, by using a projection unwrapping point recording unit of the system, the operator can set a projection unwrapping point of any single heart chamber in the cardiac image and record the projection unwrapping point.

In step four, by using a slice setting unit of the mapization unit, the operator can set a first slice and a last slice of any single heart chamber and recording the first slice, the last slice and all slices between the first slice and the last slice.

In step five, by using a division processing unit of the mapization unit, the operator can load four-chamber view images corresponding to the slices recorded by the slice setting unit into a division interface in sequential order.

In step six, through the division interface, the operator can manually perform border selection for any single heart chamber to form a sub-area in each of the loaded four-chamber view images. A sub-area processing module of the system is used to perform morphology calculation on the sub-area of each of the four-chamber view images.

In step seven, a mapped image establishment unit of the mapization is used to perform projection to unwrap the medical image of any single heart chamber into a 2D chamber map image according to the projection unwrapping point and information of all sub-areas, and express the 2D chamber map image on a chamber map display interface. The mapped image establishment unit further calculates the morphology information of all sub-areas to obtain morphology data of any single heart chamber and displays the morphology data on the chamber map display interface.

In summary, the system and method of the present disclosure has at least one of following advantages and effects.

First, by using the 3D-based cardiac image (such as the CT or MRI image) to calculate the morphology and spatial information of any single heart chamber (such as left atrium, left ventricular, right atrium, right ventricular or aortic structure), and unwrap and reconstruct the information the 3D image into the 2D chamber map display, the anatomical or functional information of any single heart chamber can be displayed on the medical image in an unwrapped plane interface, so as to provide intuitive, simple and clear images reading and interpretation.

Secondly, the system can automatically calculate morphology information including global and regional architectural information including volume and mass of any single heart chamber, myocardial wall thickness, or wall thickness heterogeneity, to form factual data and express the factual data and the mapped image of the heart chamber both on a display interface, so as to provide more intuitive, simpler and clearer images reading and interpretation.

Thirdly, the mapped image of the heart chamber can be displayed by different grayscales, different colors or different contour lines to express global and regional architectural information differences using different cut-off values including myocardial wall thickness, so that the interpreter can interpret the detailed cardiac structural/morphological data such as thinness of the chamber wall, the anatomic relationships of the blood vessels and valves more easily recognized and to notice the part in problem with ease.

Fourthly, by using the mapped images and morphological data of any single heart chamber provided by the present disclosure, the operator can discuss morphological changes of heart diseases at different timelines or with different properties, compare and understand the evolution of the heart diseases. In addition, the mapped images and morphology data information of any single heart chamber can also be used as information guide for clinical treatment intervention or treatment.

Fifthly, by using the instant calculation unit, the system can instantly calculate, analyze, quantify objectively and display morphology data of the ROI in the heart chamber map image.

BRIEF DESCRIPTION OF THE DRAWINGS

The detailed structure, operating principle and effects of the present disclosure will now be described in more details hereinafter with reference to the accompanying drawings that show various embodiments of the present disclosure as follows.

DETAILED DESCRIPTION OF THE PREFERRED EMBODIMENTS

Reference will now be made in detail to the exemplary embodiments of the present disclosure, examples of which are illustrated in the accompanying drawings. Therefore, it is to be understood that the foregoing is illustrative of exemplary embodiments and is not to be construed as limited to the specific embodiments disclosed, and that modifications to the disclosed exemplary embodiments, as well as other exemplary embodiments, are intended to be included within the scope of the appended claims. These embodiments are provided so that this disclosure will be thorough and complete, and will fully convey the inventive concept to those skilled in the art. The relative proportions and ratios of elements in the drawings may be exaggerated or diminished in size for the sake of clarity and convenience in the drawings, and such arbitrary proportions are only illustrative and not limiting in any way. The same reference numbers are used in the drawings and the description to refer to the same or like parts.

It will be understood that, although the terms 'first', 'second', 'third', etc., may be used herein to describe various elements, these elements should not be limited by these terms. The terms are used only for the purpose of distinguishing one component from another component. Thus, a first element discussed below could be termed a second element without departing from the teachings of embodiments. As used herein, the term "or" includes any and all combinations of one or more of the associated listed items.

In the embodiment, a medical image of a left atrium is mapped and unwrapped for exemplary illustration of concept of the present disclosure, but the present disclosure is not limited to be applied to the left atrium. The system and method of the present disclosure can also be applied to the left ventricular, the right atrium or the right ventricular.

Before illustration of the embodiment of the present disclosure, definitions of some terms used in the specification of the present disclosure are described first. The term "interface" is a screen shown in a displayer of a smart device (such as one of various kinds of computers) for user to watch, operate and input instruction. The term "module" is at least one program executed by the processor of the smart device to generate a desired result, or the combination of such programs. The term "unit" includes the at least one "module" and a program assembly configured to link and operate the "module" to generate a desired result. The term "system" includes a combination of above-described smart device and above-described "unit", and software/hardware assembly configured to link and operate the combination to generate a final result. The term "operator" means a person with professional medical expertise and capacity of interpreting a medical image.

Figure 1:
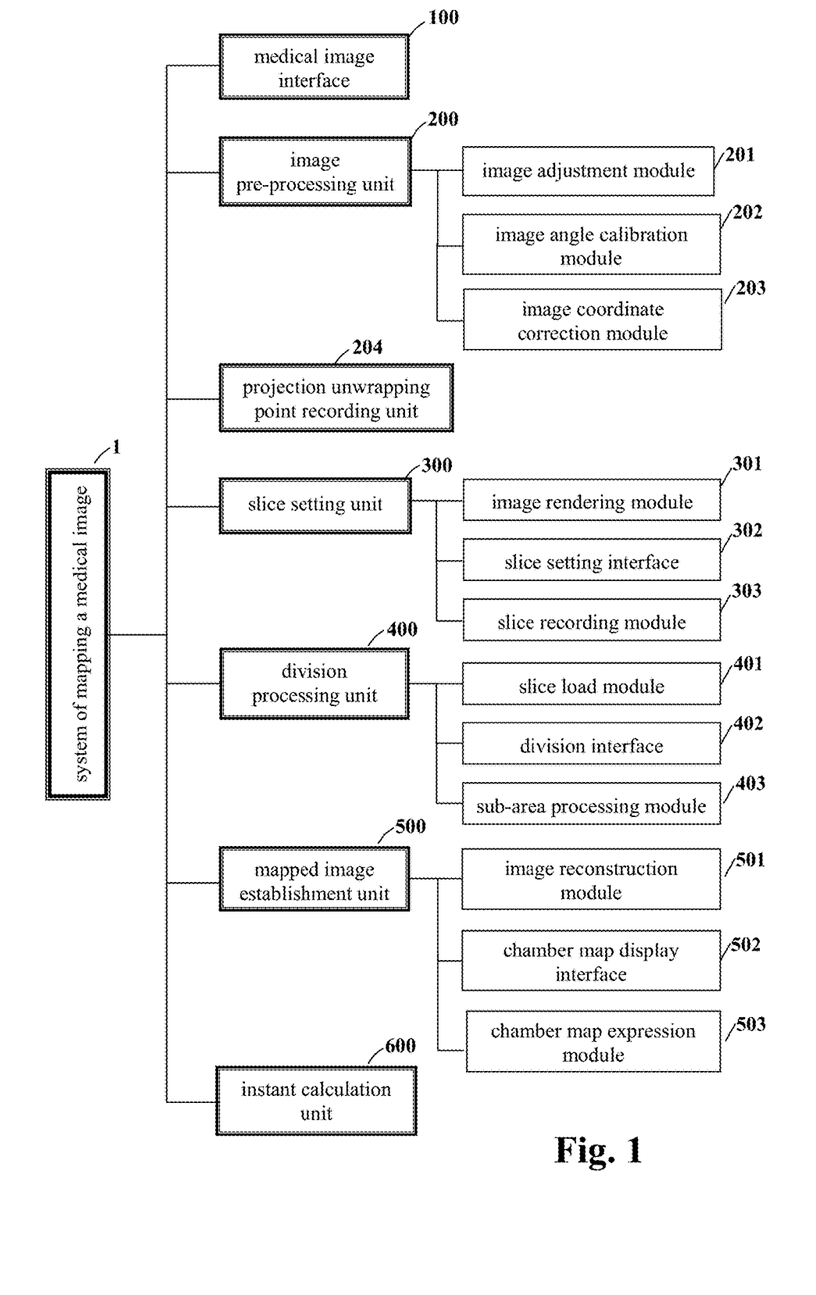
FIG. 1 is a block diagram of units and modules of a system of mapping a medical image, in accordance with the present disclosure.

Please refer to FIG. 1. The present disclosure provides a system 1 of mapping a medical image of single heart chamber, and the system includes a medical image interface 100, an image pre-processing unit 200, a projection unwrapping point recording unit 204, a slice setting unit 300, a division processing unit 400, a mapped image establishment unit 500, and a instant calculation unit 600.

The medical image interface 100 is configured to load and display a cardiac image. An image pre-processing unit 200 is configured to provide an operator to perform pre-process on the medical image shown in the medical image interface 100. The projection unwrapping point recording unit 204 is configured to provide the operator to set a projection unwrapping point of a cardiac image of a single heart chamber. The slice setting unit 300 is configured to provide the operator to set a first slice and a last slice of the cardiac image of any single heart chamber. The division processing unit 400 is configured to provide the operator to divide a single heart chamber area from the four-chamber view image of a heart. The mapped image establishment unit 500 is configured to unwrap image of any single heart chamber specified in the cardiac image into a 2D mapization image according to the processing, setting, and division results outputted from aforesaid units.

The image pre-processing unit 200 includes an image adjustment module 201, an image angle calibration module 202 and an image coordinate correction module 203. The image adjustment module 201 is configured to adjust image definition. The image angle correction module 202 is configured to adjust and correct an image angle. The image coordinate correction module 203 is configured to correct an image coordinate.

The projection unwrapping point recording unit 204 records a projection unwrapping point set by the operator. The operator sets the projection unwrapping point for any single heart chamber in the cardiac image based on the coordinate axis shown on the medical image interface 100.

The slice setting unit 300 includes an image rendering module 301, a slice setting interface 302 and a slice recording module 303. The image rendering module 301 is configured to render the image processed by the image pre-processing unit 200 into the slice setting interface 302. The slice setting interface 302 is configured to set the first slice and the last slice of any single heart chamber. The slice recording module 303 is configured to record all slices from the first slice to the last slice.

The division processing unit 400 includes a slice load module 401, a division interface 402 and a sub-area processing module 403. The slice load module 401 loads view images (mainly including four-chamber view images) into the division interface 402 according to an order of the slices record in the slice recording module 303. The operator can perform single heart chamber division on all loaded view images to form sub-areas. The sub-area processing module 403 performs morphology calculation on the each of sub-areas of the sectional images, to acquire morphology information of each of sub-areas (that is, single heart chamber).

The mapped image establishment unit 500 includes an image reconstruction module 501, a chamber map display interface 502, and a chamber map expression module 503. The image reconstruction module 501 is configured to project and unwrap any single heart chamber in the cardiac image into a 2D chamber map image according to the results of processing, setting and division performed by above-mentioned units and modules. The chamber map display interface 502 is configured to display the chamber map image. The chamber map expression module 503 is configured to express a grayscale chamber map image, a color chamber map image and a contour chamber map image.

The operations and methods of the units and modules of the present disclosure will be described in cooperation with the system interface, and the reference numbers of the units and the modules are referred to FIG. 1.

Figure 2:
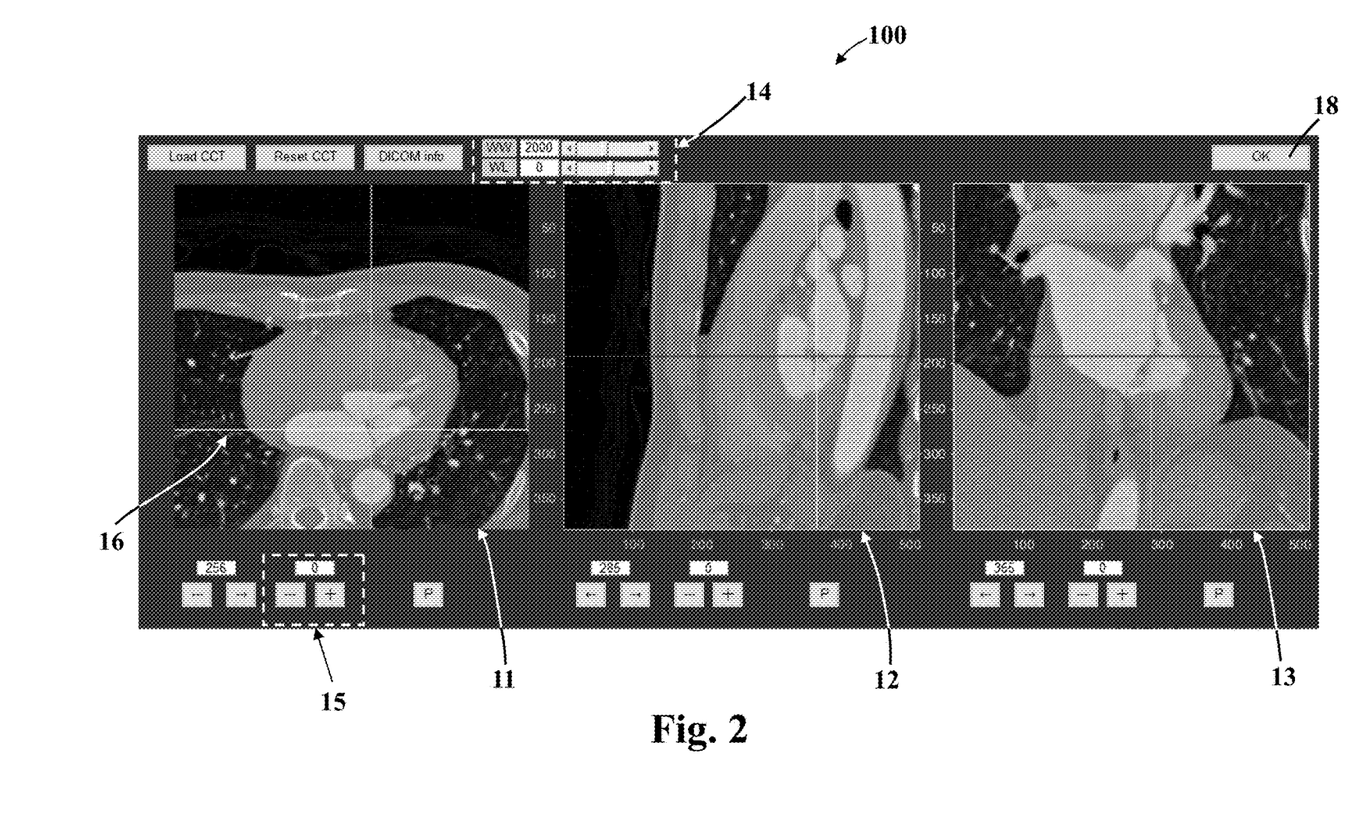
FIG. 2 is a schematic view of a medical image interface of the system of the present disclosure.

Please refer to FIG. 2. The medical image interface 100 shows a four-chamber view 11, a two-chamber view 12 and a short axis view 13 of a cardiac image.

Figure 3:
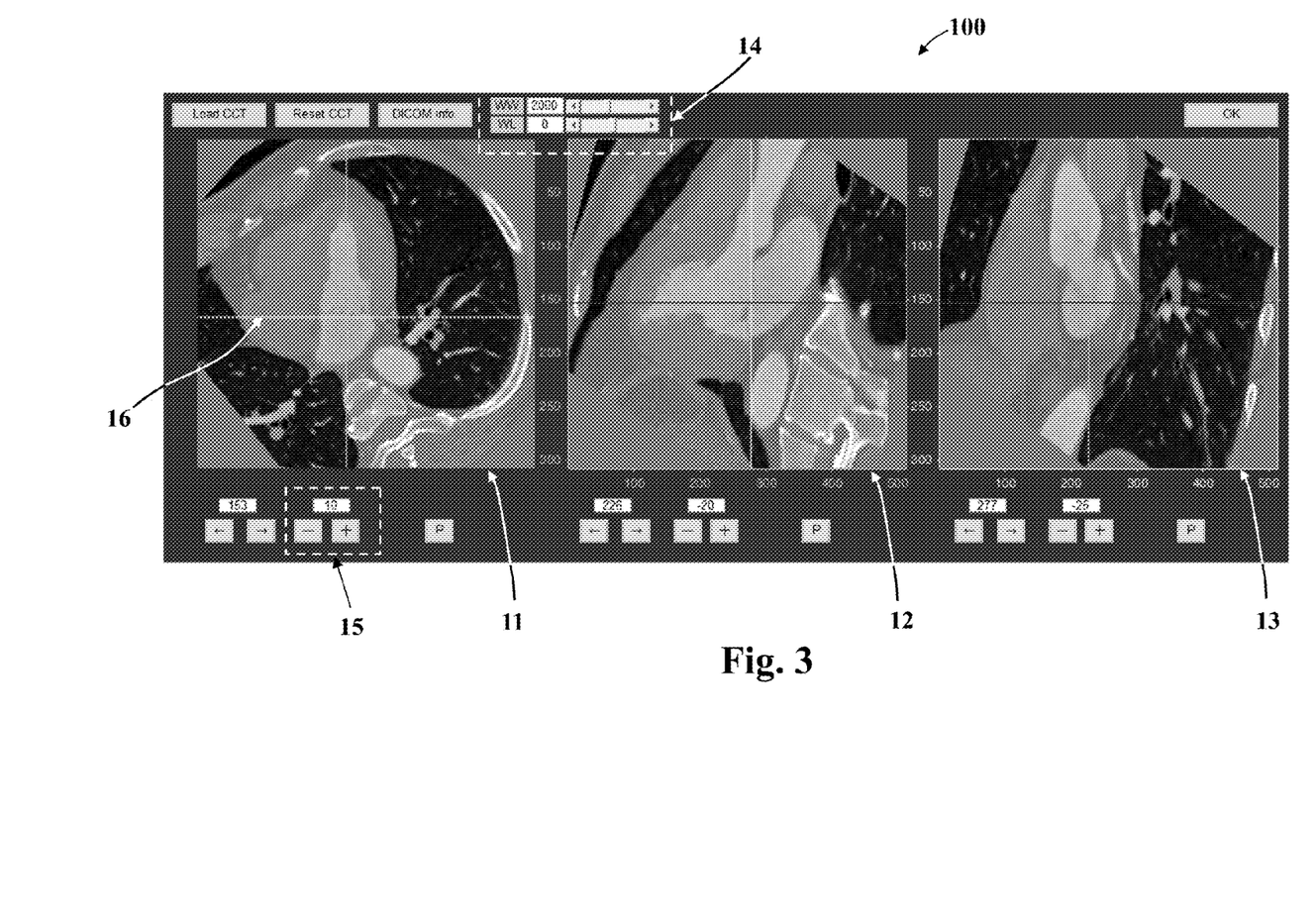
FIG. 3 is a schematic view of adjustment of a medical image of the present disclosure.

Please refer to FIG. 3. The operator can input an image adjustment instruction (such as image brightness adjustment instruction, image contrast instruction) in image adjustment fields 14 of the medical image interface 100. Upon receipt of the image adjustment instruction, the image adjustment module 201 adjusts the image to make chamber contours of each of view images clearer. The operator inputs an angle adjustment instruction into an angle adjustment field 15 of the medical image interface 100. Upon receipt of the angle adjustment instruction, the image angle correction module 202 adjusts the angle of each of view images to a desired angle. The operator inputs a coordinate correction instruction by operating a coordinate axis 16 shown in the medical image interface 10. Upon receipt of the coordinate correction instruction, the image coordinate correction module 203 corrects the image coordinate of each of the sectional images.

Figure 4:
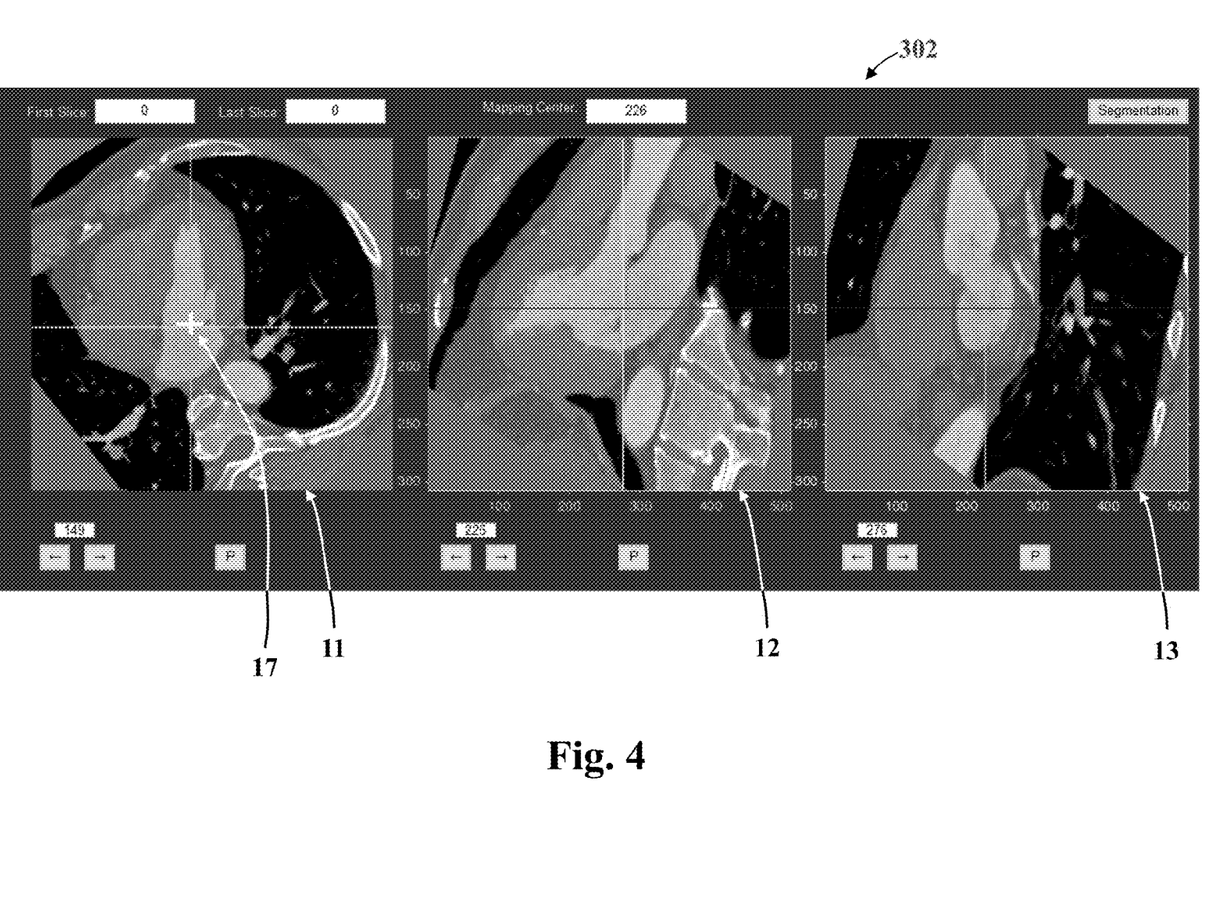
FIG. 4 is a schematic view of setting of a projection unwrapping point of the slice setting interface of the present disclosure.

Please refer to FIG. 4. After accomplishing all setting, the operator can click a switch button 18 to trigger the image rendering module 301 to convert and display the four-chamber view 11, the two-chamber view 12 and the short axis view 13 which are adjusted and corrected already, on the slice setting interface 302. Next, the operator can input a projection unwrapping point 17 based on the coordinate axis 16 shown in the four-chamber view 11. In the embodiment, the projection unwrapping point 17 is located in an area indicative of the left atrium. The projection unwrapping point recording unit 204 receives and records a coordinate of the projection unwrapping point 17.

Figure 5:
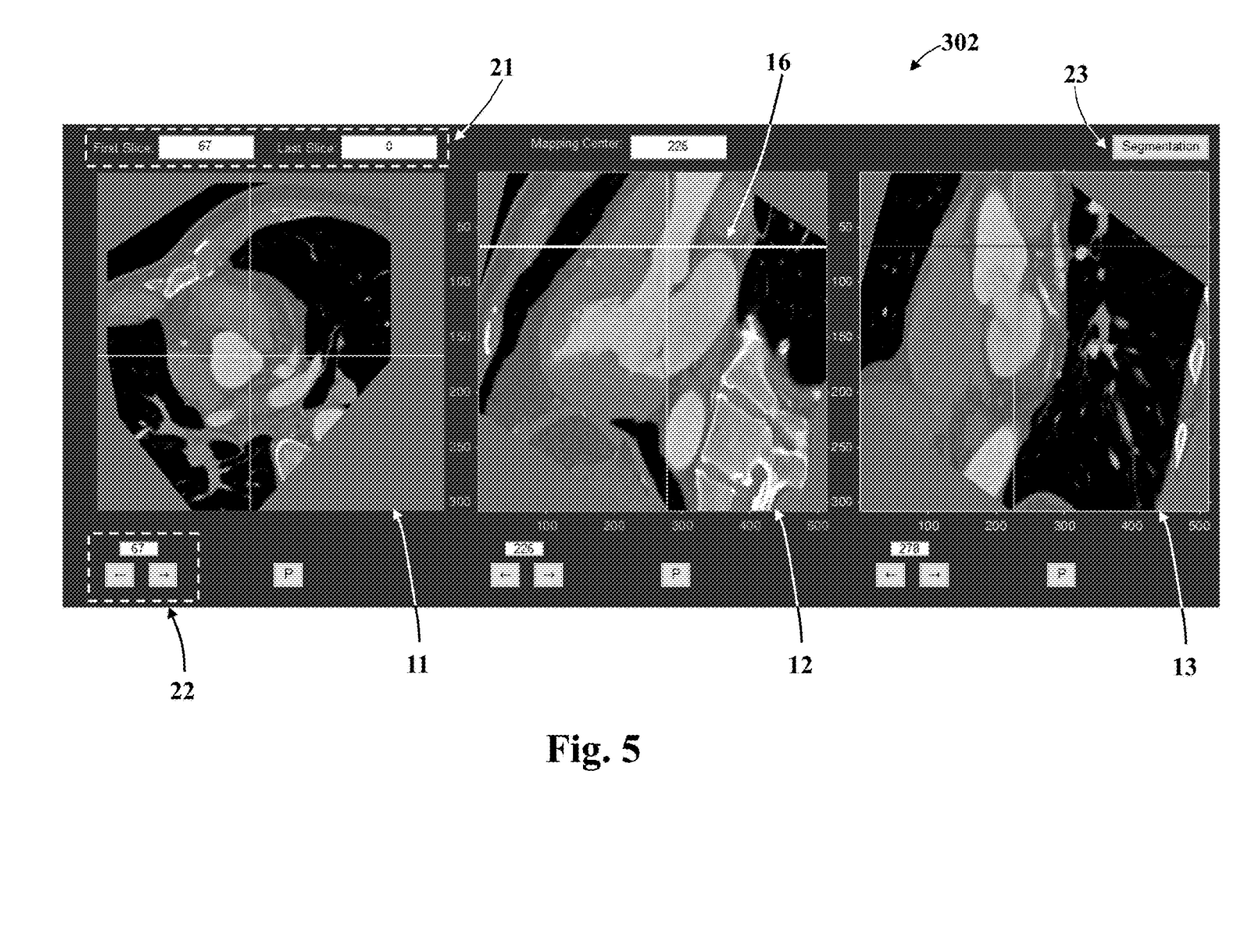
FIG. 5 is a schematic view of setting of a first slice on the slice setting interface of the present disclosure.
Figure 6:
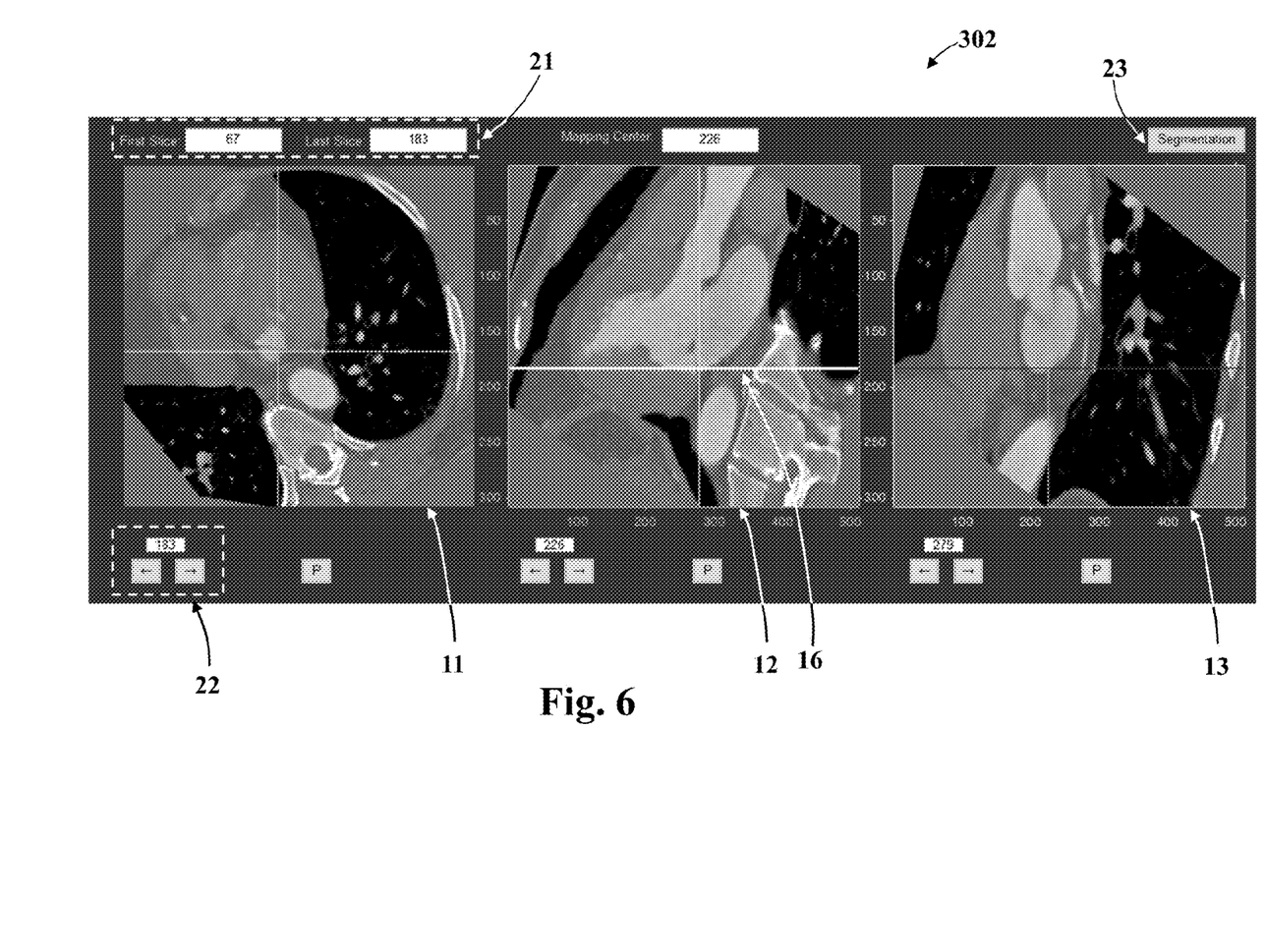
FIG. 6 is a schematic view of setting of a last slice on the slice setting interface of the present disclosure.
Figure 7:
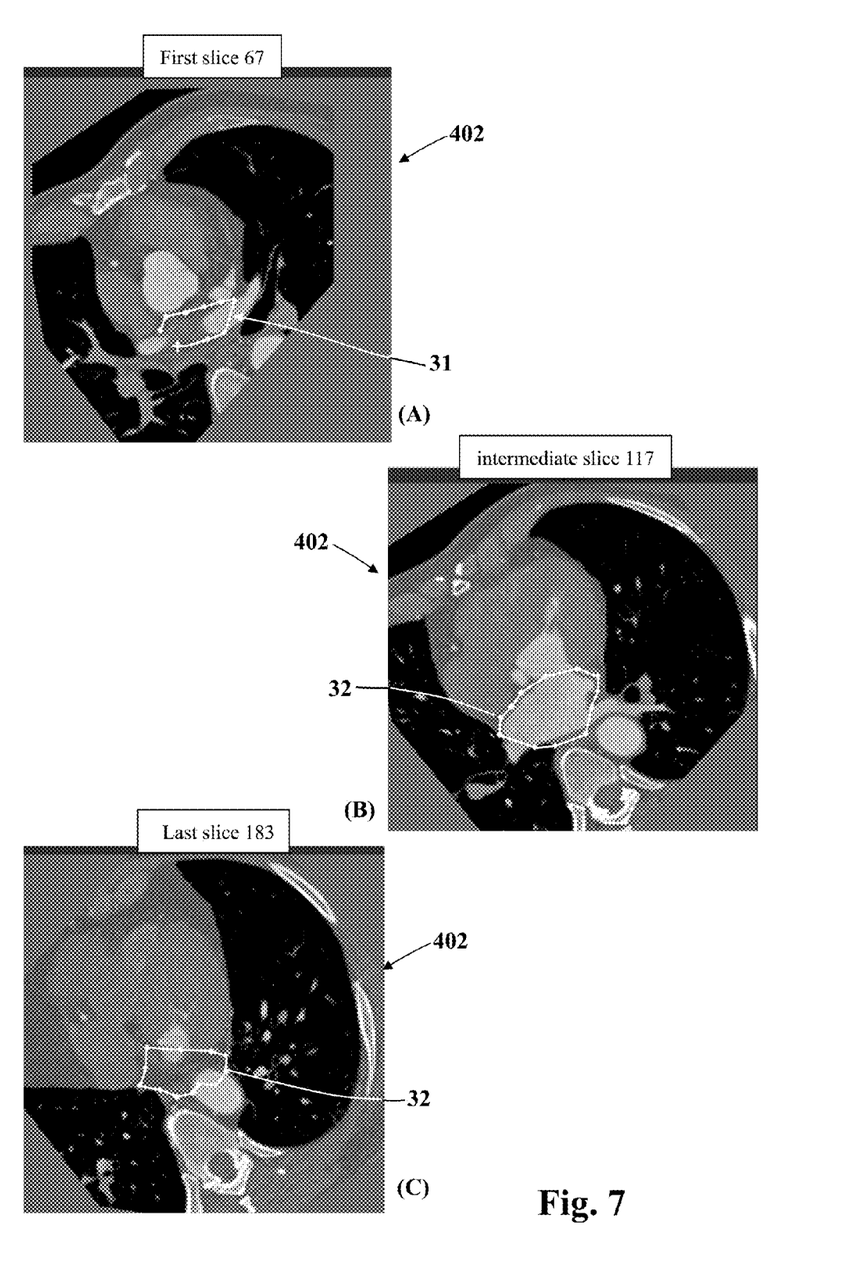
FIG. 7 is a schematic view of a division interface of the present disclosure.

Please refer to FIGS. 5 and 6. The operator can input a first slice and a last slice of the left atrium in an input field 21 of the slice setting interface 302. In the two-chamber view 12, the operator can respectively select two points on the horizontal axis of the coordinate axis 16 as first and last locations of the left atrium, so as to obtain the first slice and the last slice. Next, the operator can click direction buttons 22 to fine tune the locations and the fine-tuned locations are then inputted into the input field 21 automatically. In FIG. 7, a reference number of the first slice of the left atrium is 67, and a reference number of the last slice of the left atrium is 183. After the first slice and the last slice is inputted, the slice recording module 303 records the first slice, the last slice and all slices between the first slice and the last slice. After accomplishing to input the first slice, the last slice of the left atrium, the operator can click a division button 23 to switch the screen to the division interface 402.

As shown in FIG. 7, the slice load module 401 loads the recorded slices of the four-chamber view into the division interface 402 in sequential order. In the exemplary drawing, it is hard to show all slices between the first slice 67 and the last slice 183, so only the slices (A), (B) and (C) are shown representatively. The slice (A) is the first slice 67, the slice (B) is an intermediate slice 117, and the slice (C) is the last slice 183. The operator can use the boundary setting tool 31 provided in the division interface 402, to outline the substantial contour of the left atrium in each loaded four-chamber view image, so that the left atrium area is defined as a sub-area 32. The sub-area processing module 403 calculates inner and outer borders of the sub-area of each slice by a known technology including contour interpolation, active contour, border dilation, border shrink, seeded region grow, volume calculation, distance calculation and so on, and then according to the border information calculates a myocardial wall thickness and a chamber volume, and accumulates the chamber volumes to calculate a chamber capacity. The data obtained by above-mentioned calculation is stored. The image reconstruction module 501 of the mapped image establishment unit 500 accesses the projection unwrapping point 17 and information of all sub-areas, to unwrap the 3D medical image of the left atrium into 2D map images of the left atrium by using well-known projection method, such as geometric projection method or mathematic analysis method. The mapped image establishment unit 500 further utilizes all information of the sub-area processing module 403 to calculate and obtain the morphology data of the left atrium, such as myocardial wall thickness, volume, capacity, wall thickness heterogeneity, and morphology variation of the left atrium.

Figure 8:
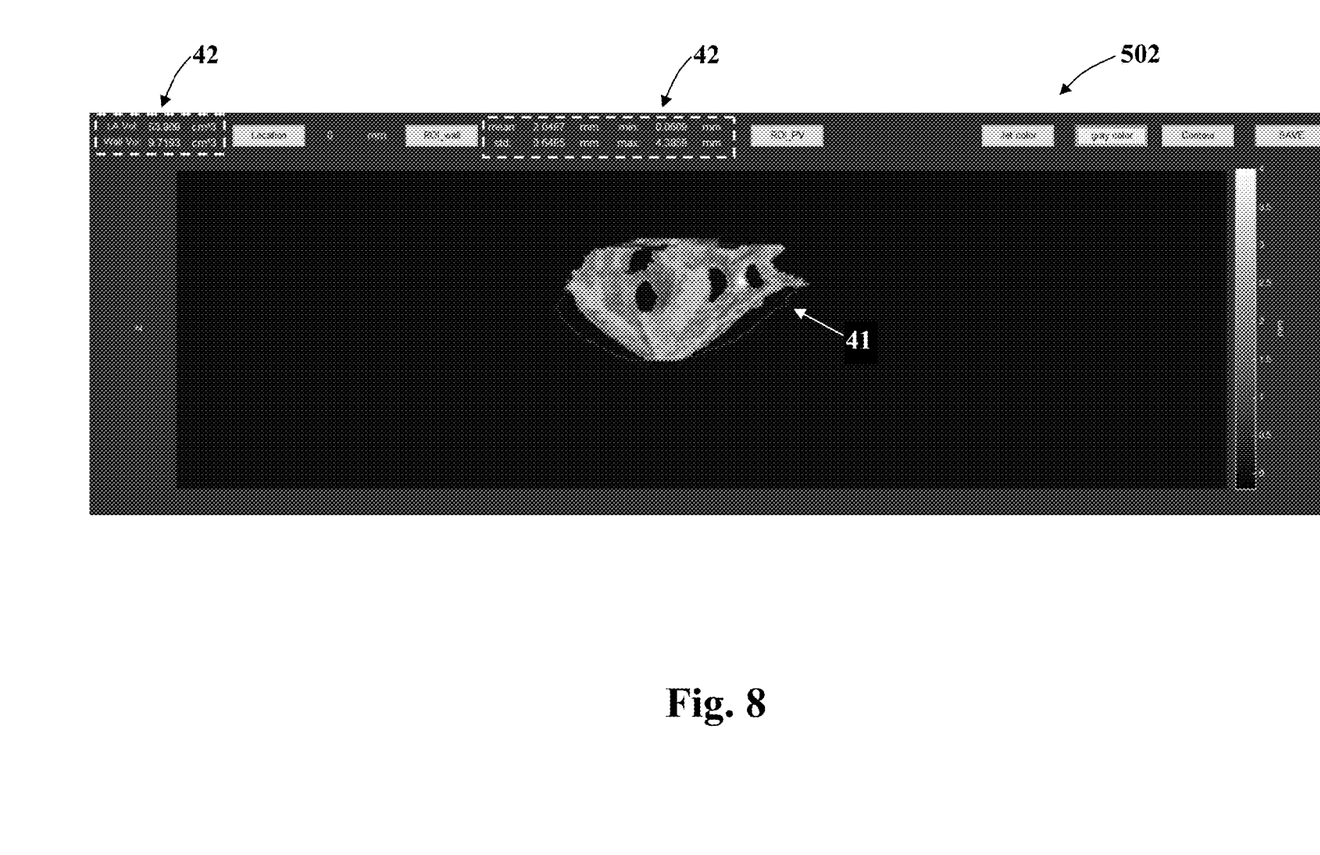
FIG. 8 is a first schematic view of a chamber map display interface of the present disclosure.
Figure 9:
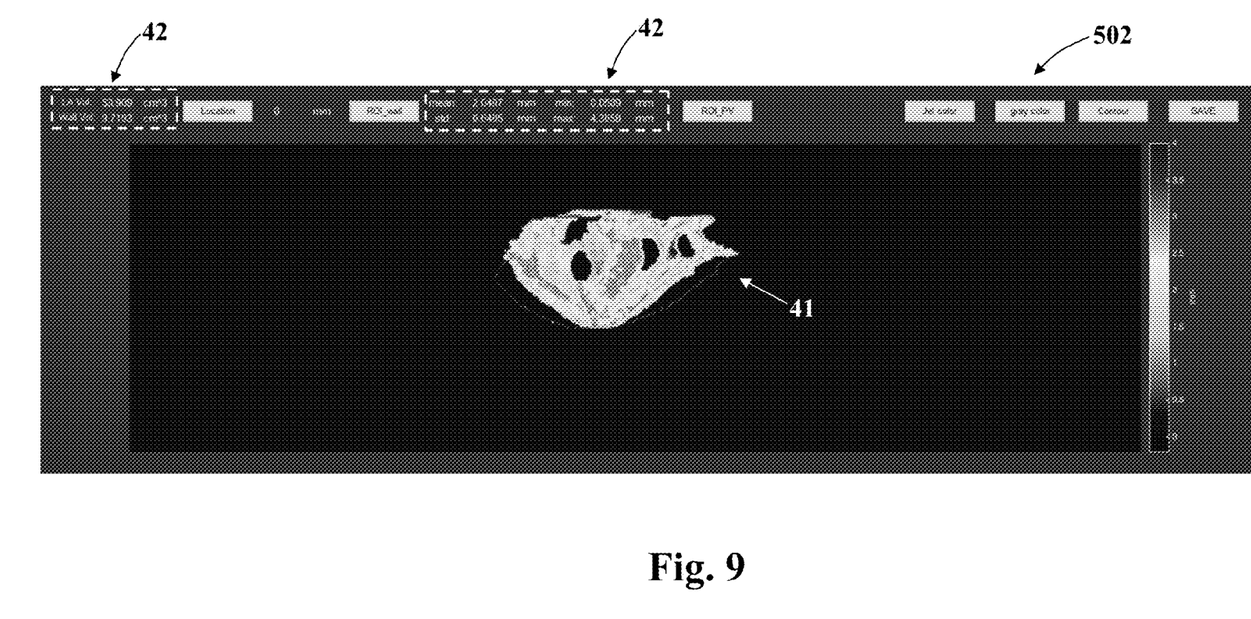
FIG. 9 is a second schematic view of the chamber map display interface of the present disclosure.
Figure 10:
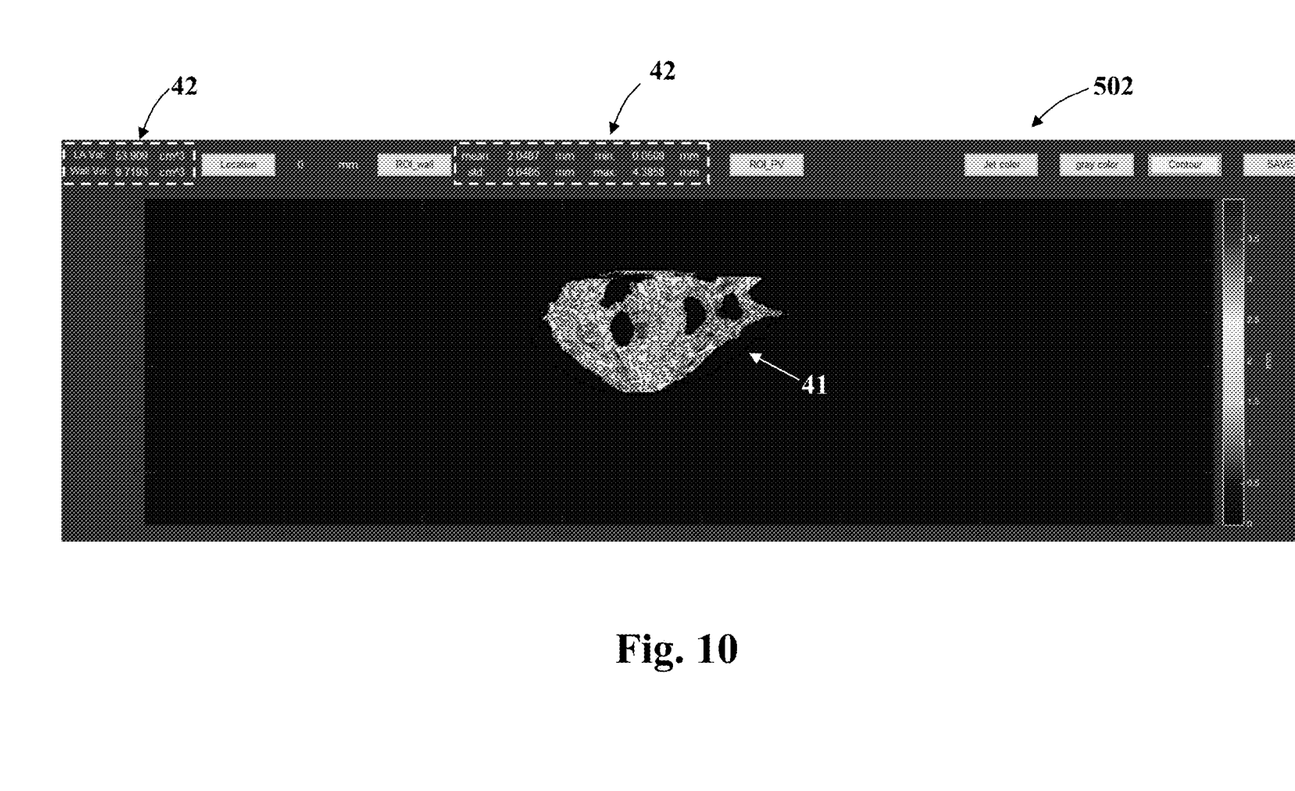
FIG. 10 is a third schematic view of the chamber map display interface of the present disclosure.

After the sub-area on the last slice is defined, the system is automatically switched to the chamber map display interface 502. Please refer to FIG. 8. The image reconstruction module 501 expresses the morphology data 42 including the map image 41 the left atrium, the volume, myocardial wall mass or myocardial wall thickness of the left atrium, on the chamber map display interface 502. The chamber map expression module 503 can express a grayscale chamber map image as shown in FIG. 8, a color chamber map image as shown in FIG. 9 and chamber contour map image as shown in FIG. 10, so as to facilitate an interpreter to interpret the thinness of the chamber wall, a location of a blood vessel, a location of a valve and so on.

Figure 11:
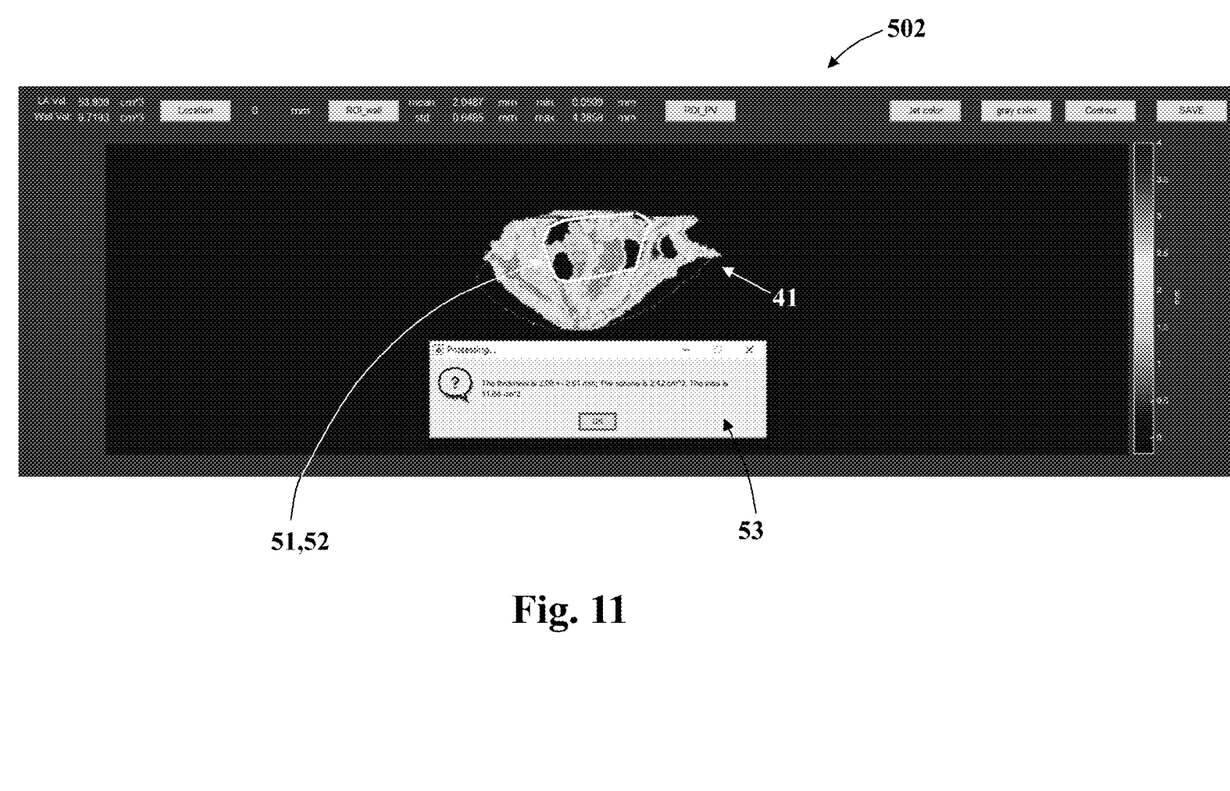
FIG. 11 is a fourth schematic view of the chamber map display interface of the present disclosure.
Figure 12:
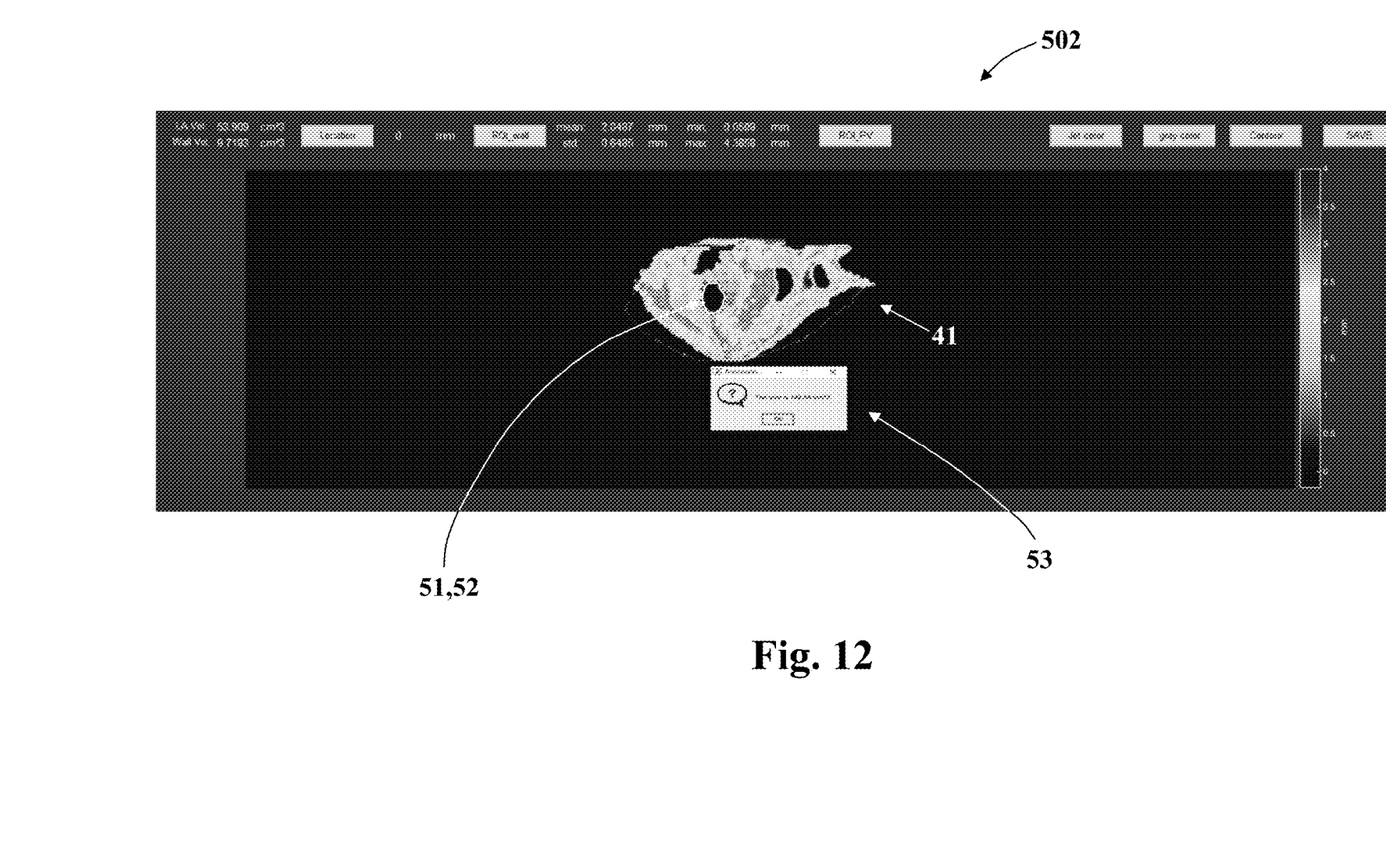
FIG. 12 is a fifth schematic view of the chamber map display interface of the present disclosure.

Please refer to FIG. 11. The operator can use a border selection tool 51 of the chamber map display interface 502 to select a region of interest (ROI) 52, and the instant calculation unit 600 then calculates morphology data related to the selected ROI instantly, and expresses the calculated morphology data 53 on the chamber map display interface 502. Please refer to FIG. 12. For example, the ROI 52 is PV-LA junction, and the instant calculation unit 600 calculates the area 53 of the PV-LA junction instantly and displays the calculated area 53 on the chamber map display interface 502.

According to the detailed descriptions for the system, the units and the modules of the present disclosure, the system can executes a method of mapping the medical image of any single heart chamber, and the method includes following steps:

In step 1, the cardiac image is loaded from a remote medical image database to the system (such as the system shown in FIG. 1) in a local smart device, and displayed on the medical image interface of the system. Preferably, the cardiac image is a CT image or a MRI image. The way of displaying the cardiac image in the medical image interface is to display the four-chamber view, the two-chamber view and the short axis view of the heart on the medical image interface.

In step 2, by using the image pre-processing unit of the system, the operator can adjust and correct brightness, contrast, angle or coordinate of each of view images on the medical image interface.

In step 3, by using the projection unwrapping point recording unit of the mapization unit, the operator can set the projection unwrapping point of the left atrium on the four-chamber view.

In step 4, by using the slice setting unit of the system, the operator can set the first slice and the last slice of the left atrium selected in the step 3, and the first slice, the last slice set by the operator, and all slices between the first slice and the last slice are recorded in the slice setting unit.

In step 5, the division processing unit of the system loads all four-chamber view images corresponding to the slices recorded in the step 4, into the division interface.

In step 6, on the division interface, the operator manually performs border selection on each of the loaded four-chamber view images, to form sub-areas of the four-chamber view images. The system then performs morphology calculation on the sub-area of each of sectional images by using the sub-area processing module.

In step 7, by using the mapped image establishment unit, the system accesses the projection unwrapping point and the information of all sub-areas, and then unwraps the 3D medical image of the left atrium into 2D map images of the left atrium by a projection method according to the projection unwrapping point and the information of all sub-areas, and expresses the 2D map image on the chamber map display interface. The mapped image establishment unit further performs calculation according to the morphology information of all sub-areas to obtain the morphology data of the left atrium which is then displayed on the chamber map display interface.

In the step 7, the system can further express the grayscale chamber map image, color chamber map image and chamber contour map image by using the chamber map expression module 503.

The above-mentioned descriptions represent merely the exemplary embodiment of the present disclosure, without any intention to limit the scope of the present disclosure thereto. Various equivalent changes, alternations or modifications based on the claims of present disclosure are all consequently viewed as being embraced by the scope of the present disclosure.

What is claimed is:

1. A system of mapping a cardiac image of single heart chamber, comprising:
   a medical image interface configured to display a cardiac image acquired from a medical 3D-based image database;
   an image pre-processing unit configured to provide an operator to process and correct image brightness, contrast, an angle alignment or coordinate of the cardiac image displayed in the medical image interface;
   a projection unwrapping point recording unit configured to record a projection unwrapping point set by the operator for any single heart chamber by operating a coordinate axis of the medical image interface;
   a slice setting unit comprising an image rendering module, a slice setting interface and a slice recording module, wherein the image rendering module is configured to render the cardiac image processed by the image pre-processing unit into the slice setting interface, to provide the operator to set a first slice and a last slice of any single heart chamber in the slice setting interface, wherein the slice recording module is configured to record the first slice, the last slice and slices between the first slice and the last slice;
   a division processing unit comprising a slice load module, a division interface and a sub-area processing module, wherein the slice load module is configured to load four-chamber view images corresponding to the recorded slices into the division interface, to provide the operator to divide an area of any single heart chamber from each of the four-chamber view images in the division interface, and the divided area of any single heart chamber is defined as a sub-area, wherein the sub-area processing module is configured to calculate each of the sub-areas according to a pre-determined function, to obtain an inner border, an outer border and morphology information of each of the sub-areas; and
   a mapped image establishment unit comprising an image reconstruction module and a chamber map display interface, wherein the image reconstruction module is configured to unwrap a 3D cardiac image of any single heart chamber into a 2D chamber map image of any single heart chamber by using projection manner and according to the projection unwrapping point and information of all of the sub-areas, and calculate the morphology information to obtain morphology data of any single heart chamber, wherein the chamber map display interface is configured to display the chamber map image and the morphology data.

2. The system according to claim 1, wherein the cardiac image is a CT image or a MRI image.

3. The system according to claim 1, wherein the cardiac image shown on the medical image interface comprises a four-chamber view, a two-chamber view and a short axis view.

4. The system according to claim 1, wherein the image pre-processing unit comprises an image adjustment module, an image angle correction module and an image coordinate correction module, and the image adjustment module is configured to receive an image adjustment instruction inputted by the operator through the medical image interface, and performs image adjustment according to the image adjustment instruction to make the chamber contour of the cardiac image clearer;
   wherein the image angle correction module is configured to receive an angle adjustment instruction inputted by the operator through the medical image interface, and adjust the cardiac image to a desired angle according to the angle adjustment instruction;
   wherein the image coordinate correction module is configured to receive a coordinate correction instruction inputted by the operator through the medical image interface, and correct an image coordinate of the cardiac image according to the coordinate correction instruction.

5. The system according to claim 1, wherein any single heart chamber is one of a left atrium, a right atrium, a left ventricular, a right ventricular of a heart.

6. The system according to claim 1, wherein the mapped image establishment unit further comprises a chamber map expression module configured to express the chamber map image in the chamber map display interface by a grayscale chamber map image, a color chamber map image or a chamber contour map image.

7. The system according to claim 1, further comprising an instant calculation unit configured to calculate and display morphology data of an ROI of the chamber map image, and the ROI is selected by the operator instantly.

8. The system according to claim 1, wherein the morphology data comprises a chamber volume, a chamber wall volume or a chamber wall thickness, and the chamber wall thickness further comprises a homogenization value, an average thickness, a maximal thickness or a minimal thickness.

9. A method of mapping a cardiac image of single heart chamber, comprising:
   - acquiring a cardiac image from a remote medical image database, loading the medical image into a system in a local smart device, and displaying the medical image in a medical image interface of the system;
   - adjusting and correcting brightness, contrast, angle or coordinate of each of view images in the medical image interface by using an image pre-processing unit of the system;
   - setting a projection unwrapping point of any single heart chamber in the cardiac image and recording the projection unwrapping point, by using a projection unwrapping point recording unit of the system;
   - setting a first slice and a last slice of any single heart chamber and recording the first slice, the last slice and all slices between the first slice and the last slice, by using a slice setting unit of a mapization unit;
   - loading four-chamber view images corresponding to the slices recorded by the slice setting unit into a division interface in sequential order, by using a division processing unit of the mapization unit;
   - manually performing border selection for any single heart chamber to form a sub-area in each of the loaded four-chamber view, through the division interface;
   - performing morphology calculation on the sub-area of each of the four-chamber view images to obtain sub-area information by automatic algorithm, by using a sub-area processing module of the system;
   - performing projection to unwrap a 3D medical image of any single heart chamber into a 2D chamber map image according to the projection unwrapping point and information of all of the sub-areas and expressing the 2D chamber map image on a chamber map display interface, by using a mapped image establishment unit of the mapization; and
   - calculating each morphology information of all of the sub-areas to obtain morphology data of any single heart chamber and displaying the morphology data on the chamber map display interface.

10. The method according to claim 9, wherein the cardiac image is a CT or a MRI image.

11. The method according to claim 9, wherein the step of displaying the medical image comprises: displaying a four-chamber view, a two-chamber view and a short axis view of the medical image in the medical image interface.

12. The method according to claim 9, wherein the step of expressing the 2D chamber map image on a chamber map display interface further comprises:
   - expressing the chamber map image in grayscale, color or contour line, by using a chamber map expression module of the system.

13. The method according to claim 9, wherein any single heart chamber is one of a left atrium, a right atrium, a left ventricular and a right ventricular of a heart.

* * * * *